(12) United States Patent
Weber et al.

(10) Patent No.: US 6,306,119 B1
(45) Date of Patent: Oct. 23, 2001

(54) SKIN RESURFACING AND TREATMENT USING BIOCOMPATIBLE MATERIALS

(75) Inventors: Paul J. Weber, Ft. Lauderdale; Michael R. Weber, Tampa, both of FL (US); Luiz B. Da Silva, Danville, CA (US)

(73) Assignee: Pearl Technology Holdings, LLC, Clearwater, FL (US)

( * ) Notice: Subject to any disclaimer, the term of this patent is extended or adjusted under 35 U.S.C. 154(b) by 0 days.

(21) Appl. No.: 09/234,224

(22) Filed: Jan. 20, 1999

(51) Int. Cl.$^7$ .................................................. A61M 35/00
(52) U.S. Cl. ............................................ 604/290; 606/131
(58) Field of Search ................................ 604/68–72, 140, 604/143, 289, 290, 313; 606/131

(56) References Cited

U.S. PATENT DOCUMENTS

| | | |
|---|---|---|
| 3,815,286 | 6/1974 | Piet . |
| 3,945,379 * | 3/1976 | Pritz et al. ............................. 604/70 |
| 5,037,431 | 8/1991 | Summers et al. ..................... 606/131 |
| 5,620,414 | 4/1997 | Campbell, Jr. ......................... 604/22 |
| 5,810,842 | 9/1998 | Di Fiore et al. ..................... 606/131 |
| 5,971,999 | 11/1999 | Naldoni ................................. 606/131 |
| 6,080,165 | 6/2000 | DeJacma .............................. 606/131 |

FOREIGN PATENT DOCUMENTS

| | | |
|---|---|---|
| 0258901A2 | 3/1987 | (EP) . |
| 0324448A1 | 11/1989 | (EP) . |
| 0550943A1 | 10/1992 | (EP) . |
| 0564392A2 | 3/1993 | (EP) . |
| 0806184A1 | 9/1997 | (EP) . |
| 0992221A2 | 6/1999 | (EP) . |
| WO 97/11650 | 4/1997 | (WO) . |
| WO 99/20336 | 4/1999 | (WO) ........................... A61M/35/00 |
| WO 99/37229 | 7/1999 | (WO) . |
| WO 99/37299 * | 7/1999 | (WO) . |

* cited by examiner

Primary Examiner—Anhtuan T. Nguyen
(74) Attorney, Agent, or Firm—John P. Wooldridge

(57) ABSTRACT

Biocompatible materials are propelled at the skin with sufficient velocity to cause desired resurfacing of skin layers to the desired penetration depth. The materials, such as dry ice or water ice, are harmonious with the human body and thus eliminate foreign body reactions. Various materials may be used in combination, including local anesthetics and vasoconstrictors in solid or liquid form. The biocompatible solid or liquid particles are suspended in a cold carrier fluid and propelled through an insulated delivery system to the surface of the skin. The treatment of diseased skin lesions may be accomplished using the present invention as a drug delivery system.

17 Claims, 2 Drawing Sheets

SKIN RESURFACING AND TREATMENT USING BIOCOMPATIBLE MATERIALS

BACKGROUND OF THE INVENTION

1. Field of the Invention

The present invention relates to the resurfacing or treatment of skin using biocompatible materials in a droplet or crystalline form that are propelled into the surface of the skin.

2. Description of Related Art

Resurfacing the human skin can be achieved by several mechanisms that are aimed primarily at disrupting the epidermal and upper dermal layers. Human skin is composed of at least three layers of variable thickness, depending upon body location. The uppermost layer, or epidermis, is usually as thin as a sheet of paper. The layer just below the epidermis is the dermis, which is largely composed of collagen and makes up the "leather" layer of the skin. The dermis may vary in thickness from that of paper (50–100 $\mu$m) to as thick as half an inch on the neck and back. The layer below the dermis may be composed of either muscle (around the eyes and mouth) or fat, otherwise known as subcutaneous fat.

New human surface skin is regenerated following resurfacing by the surrounding islands of normal epidermis and epidermal cells migrating from the deep hair pores and other pore structures that permeate the upper dermis, mid dermis, and epidermis. If excessive scar tissue, rather than a plethora of epidermal cells, closes a surface wound, then an unsightly scar will result. The key to all resurfacing procedures is a controlled destruction of the desired area that still allows the regeneration of new tissues from pores and neighboring islands of untouched, untreated skin.

The procedures currently used in human skin resurfacing include chemical peeling, dermabrasion, laser surgery, and most recently the "power peel" or crystalline peel. In chemical peeling, a caustic, disruptive or destructive liquid agent is applied to the surface skin to damage existing epidermal and dermal cells, which will then be replaced by the body. Peeling agents act depending on their strength and type. Examples of chemical peeling agents include fruit acid peel, glycolic acid peel, and trichloracetic acid (TCA) and phenol peels. TCA peels can be made to act at deeper and varying depths by varying the concentration of TCA used to destroy the surface skin. Concentrations as low as 5–10% TCA will behave similarly to a fruit acid peel, and concentrations of 50% TCA may cause severe peeling burns, which simulates phenol, and may border on scarring. Phenol, when diluted with water, penetrates more deeply and destroys more tissue than most other peeling agents.

Dermabrasion literally means abrasion of the skin and is a procedure in which a rotating sanding wheel, or abrasive substance, is applied to a rigidified skin to sand out an undesirable feature, mark, or scar. Some high-speed dermabrasion rotors go up to 200,000 revolutions per minute (rpm) and do not require any rigidity to the tissues; however, they require extremely skilled personnel and special instrumentation and are impractical for most office use. A minor mistake with such a high powered machine can have disastrous results. Dermabrasion is usually performed with a rotating wheel operating at speeds under 10,000 rpm after the skin has been rigidified using freon or dichlorotetrafluoroethane. In dermabrasion (unlike laser surgery), the person operating the abrading wheel has a direct tactile sense of pressing the wheel into the tissues being treated and can apply differential pressure to areas of elevation. Dermabrasion can be achieved to various depths depending upon the depth of freezing (rigidification), the number of passes of the abrader, the type of abrasive wheel, and the pressure applied. This procedure is waning in use, however, due to the unavailability of freon.

Laser surgery has recently become popular to remove or reduce wrinkles, remove tumors, and alter scars, although results are mixed. Several types of lasers are used, including carbon dioxide and erbium-YAG lasers. Carbon dioxide lasers deliver light radiation at 10 $\mu$m, which can vaporize and destroy surface skin. These lasers may be set on various pulse patterns to deliver precise and controlled amounts of laser radiation to the skin in a relatively uniform and homogenous fashion across the surface. An unfortunate disadvantage of this laser is that heat can be transmitted to the surrounding tissues. Additionally, after the first pass of the carbon dioxide laser, the skin begins to ooze and become wet at the surface as fluids build up in response to the damage. Since water and blood absorb in the infrared region, a second pass of the laser will penetrate to a variable depth, depending on how much surface ooze there is in the area. The ooze prevents the laser energy from reaching the target tissues uniformly. During laser irradiation, the tissues may begin to desiccate, which ultimately results in severe thermal damage. Depositing too much laser energy on the target tissues can result in persistent redness, scarring, and other complications or damage, even with thermal relaxation techniques to mitigate heat transfer.

Although other lasers, such as the erbium-YAG laser or combination $CO_2$/erbium laser, were developed in an attempt to reduce bleeding and thermal damage, serious scarring and persistent redness can still result. If the penetration depth of the damage is complete and the regenerating skin structures are destroyed, scarring will ensue. Scarring is the unwanted presence of large amounts of collagen in the upper surface, with a minimal amount of normal appearing epidermis to lend a normal appearance to the skin. When scars are treated with certain lasers, the light does not actually remove or destroy collagen, but usually affects the hemoglobin and other blood pigments. The reduction of blood vessels to the scar causes an optical effect that makes the scar less noticeable.

The power peel is relatively new in the United States and is basically a method of "sandblasting" the skin. This procedure has been touted to reduce acne scars and remove all other types of scars and imperfections. The power peel is a process by which aluminum oxide crystals, which are extremely hard, are shot at the skin with 25 psi of air pressure. Safe operation of these devices requires the use of a limited number of passes or accurate control of pass speed to the target area. A power peel that only removes the epidermis of the skin will not result in any alteration of scar formation and produces very little long-lasting cosmetic effect. However, aluminum oxide crystals that are shot deeply enough into the skin to remove or alter deeper structures such as scars or pits can cause granuloma formation or foreign body reaction because aluminum oxide crystals are not biocompatible. Thus the body extrudes or encapsulates unwanted particles at levels of skin where protection is necessary, which may lead to disease and unsightly scarring. Even systems that include a vacuum apparatus to suck away unwanted particles do not remove 100% of the particles. Even a small amount of residue crystals can lead to disease and other cellular difficulties.

Thus, it would be advantageous to develop a procedure that can remove scars, wrinkles, and various other imperfections or lesions on the skin without introducing foreign bodies or substances that cause adverse physiological reactions or produce thermal damage. The present invention addresses this problem by using materials that are harmonious with the human body.

SUMMARY OF THE INVENTION

The present invention is a method and apparatus for resurfacing or treating the skin using biocompatible, non-toxic materials that are propelled at the skin with sufficient velocity to cause destruction or loosening of tissues to the desired depth upon impact. One objective of the invention is to blast materials into the skin that are harmonious with the human body and thus do not cause foreign body reactions, which lead to granulomas and scarring. The materials must be hard enough (crystalline) or propelled at high enough velocities to penetrate to the appropriate depth in the dermis to remove unwanted skin features. Suitable resurfacing materials include solid carbon dioxide (dry ice) and ice ($H_2O$); organic materials such as urea, or other amines (including amino acids) or amides; organic polymers such as sugars, carbohydrates, or proteins; and inorganic salts such as phosphates, sulfates, carbonates and nitrates. To relieve pain, a local anesthetic may be used separately or in combination with the biocompatible materials used to resurface the skin. Antibiotics could be included to prevent infection; bioabsorbable or biodegradable compounds or drugs can be delivered to the skin to treat diseases. Vasoconstrictors, such as adrenaline, can be placed into crystalline form and fired into the skin to constrict blood vessels on the surface of the skin to prevent bleeding.

The biocompatible materials are suspended in a carrier fluid (e.g., a cold gas) that is under pressure and propelled through an insulated delivery tube to a delivery tip or nozzle to the surface of the skin. A vacuum system in conjunction with the delivery system is advantageous to remove excess materials or reaction by-products that build up on the surface of the skin. The biocompatible crystals or droplets are maintained at the proper temperature (e.g., freezing) in the delivery system. Initially, the biocompatible materials are contained in a holding tank, and particles of the appropriate size are generated using various means, including grinding or sonication. Alternatively, resurfacing particles are formed by spraying microdroplets of the desired substance or mixture via jets or nozzles into a cold carrier fluid, which freezes or cools the droplets (aerosol). The biocompatible particles are forced through the delivery system by the carrier fluid, such as dry air or $N_2$, and shot into the skin surface at the desired velocity.

The temperature and flow of the carrier gas and biocompatible particles are monitored and maintained at the proper temperature and flow rate, so as to propel unmelted crystals or cold droplets at the skin at the desired velocity. Other monitoring devices for skin temperature, pressure sensing at the delivery tip, and penetration depth are useful with feedback systems to optimize the delivery of crystals or droplets to the skin surface.

An objective of the present invention is to provide a method and apparatus to remove scars, wrinkles, and other imperfections of the skin without introducing foreign bodies or substances that cause adverse physiological reactions or produce thermal damage. Another objective of the invention is to provide a delivery system for delivering or depositing drugs in solid or liquid form at the desired depth in the epidermis or dermis for treatment of diseased skin lesions, e.g., pre-cancers. Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

Figure 1:
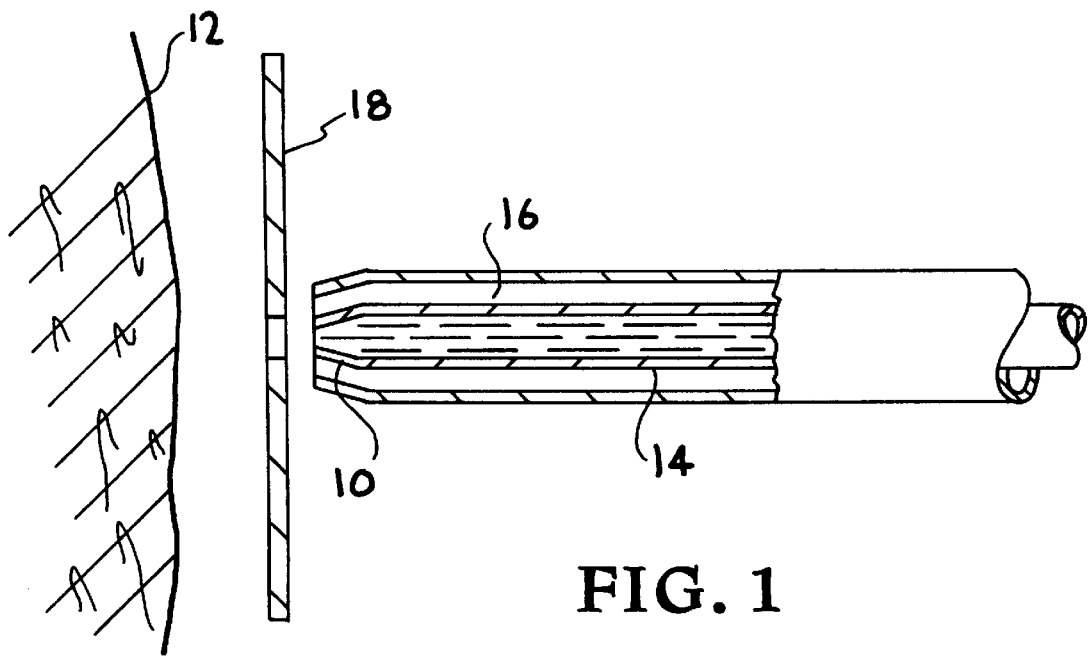
FIG. 1 shows the method of the present invention where the biocompatible crystalline materials are propelled through a delivery tip to the skin surface.

The present invention is a method and apparatus for resurfacing or treating the skin using biocompatible materials that are blasted at the skin with sufficient velocity to cause destruction, loosening, or unbinding of tissues to the desired depth upon impact. The penetration depth of the particles is controlled by the operator. The materials that are propelled into the skin are non-toxic and harmonious with the human body and thus do not cause foreign body reactions, which may lead to granulomatous disease and/or scarring. The materials must be hard enough (crystalline) or propelled forcefully enough to penetrate to the appropriate depth in the dermis to remove unwanted skin features. Suitable materials include solid carbon dioxide (dry ice) and ice ($H_2O$); organic materials such as urea, or other amines (including amino acids) or amides; organic polymers such as sugars, carbohydrates, or proteins; and inorganic salts such as phosphates, sulfates, carbonates and nitrates. These materials can be used separately or in combination.

Several considerations are taken into account in the choice of skin resurfacing materials. Biocompatible materials are defined for purposes of this description as materials that can be propelled into the epidermal or dermal layers of the skin without significant adverse biological (i.e., toxic, inflammatory, carcinogenic, or immunogenic) host response (e.g., foreign body reaction, autoimmune disease, necrosis, apoptosis). The materials may be in a solid (crystalline) or liquid form. The materials are preferably at low temperatures (e.g., <0° C.), although too cold of a material can result in unacceptable tissue death. Human tissues can safely tolerate freezing with ice to a certain extent, for a limited amount of time, before frostbite occurs. Materials may be used that become volatile as gas or change from a solid to a liquid at temperatures warmer than about −20° C.

Other biocompatible materials or additives that have an additional function to impart to the skin can be used in combination with the resurfacing materials, and may be particularly useful in cases where deeper tissue alteration is needed. For example, once the epidermis is penetrated by any surface destructive procedure, pain will result when the dermal nerves are stimulated. To relieve this pain, crystalline local anesthetic such as xylocaine (lidocaine) or any number of topical or local anesthetics could be used, either separately or in combination with other materials. These local anesthetics will dissolve and be carried to the dermal nerves upon impacting the serum of the skin. Additionally, vasoconstrictors or blood vessel closing agents as adrenaline could be used in solid or droplet form and fired into the skin to constrict blood vessels on the surface of the skin to prevent bleeding, which is a common problem with many forms of skin resurfacing (i.e., dermabrasion. laser). Less bleeding also results if the procedure is performed at deeper skin levels. Buffering agents or hydrophilic materials to absorb surface water could also be useful, and antibiotics could be added to prevent infection.

The present invention may be used as a drug delivery system with bioabsorbable or biodegradable compounds or drugs propelled into the surface of the skin. Biodegradable polymeric systems can be used for drug delivery and offer greater flexibility in the design of delivery systems for large molecular weight drugs, such as peptides and proteins. Biocompatible gels, like hydrogels, can be grafted onto other biomaterials with good mechanical properties for skin resurfacing. The combination can accomplish both skin resurfacing and drug delivery in the epidermis and dermis. Water insoluble polymers such as poly(glycolic acid) have been investigated as biodegradable drug delivery systems.

For dermatological applications, the present invention may be used to deliver drugs for treatment of pre-cancerous or cancerous lesions in the epidermis and dermis. The topical delivery of certain medicines often cannot penetrate deeply or uniformly enough, and long-term topical application of the creams or gels is inconvenient for the patient. To achieve long-lasting, deeper skin treatment for lesions, drugs (e.g., 5-fluorouracil) in a crystal or gel form may be shot into the skin to penetrate the deep epidermis.

FIG. 1 shows the method of the present invention where the biocompatible particles are suspended in a carrier fluid and propelled through a delivery tip or nozzle 10 to the surface 12 of the skin with a delivery velocity sufficient to achieve the desired penetration depth or skin effect. The pressure of the carrier fluid in the delivery system is typically about 25 psi. The delivery tube 14 may include a vacuum tube 16 with an opening located near the tip 10 to remove excess materials or reaction by-products that build up on the surface 12 of the skin. A shield 18 to protect surrounding tissues and the operator can be included to reduce the spattering of fluids and tissues during the dermal passes. The delivery tube 14 is insulated to maintain the biocompatible crystals or droplets at the proper temperature (e.g., freezing).

Figure 2:
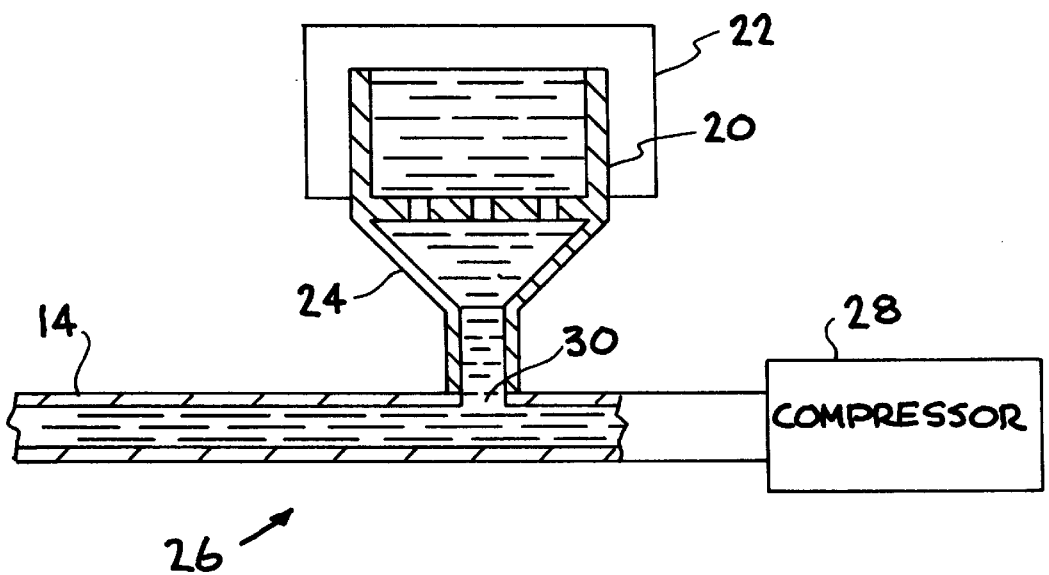
FIG. 2 shows an embodiment of an apparatus for forming solid biocompatible materials and propelling them into the delivery system.

FIG. 2 shows an illustrative embodiment of an apparatus for containing solid biocompatible materials and propelling them into the delivery tube 14. The materials, such as carbon dioxide or water (with possible additives such as local anesthetic and adrenaline), are introduced into a temperature-controlled holding tank 20. Temperature control, specifically cooling, may be achieved by a variety of cooling means 22, such as a refrigerator unit or liquid nitrogen external cooling tank surrounding the holding tank. The cooling means can reduce the temperature of the biocompatible materials used below their freezing points and/or maintain the desired temperature. Preservatives (e.g., benzyl alcohol, methylparaben) could be added to the mixture of resurfacing materials (and other additives) to prevent bacterial formation and to maintain a sterile environment.

Crystalline particles of the appropriate size and uniform consistency are created from the solid materials in the holding tank 20. The particles should be of a sufficient or optimum size for maximum impact upon the skin (e.g., <250 $\mu$m, more typically <150 $\mu$m). The biocompatible materials may be ground into the desired particle size(s) using mechanical means (e.g., grinder, pulverizer) or ultrasonic methods (e.g., sonicator). To achieve the necessary particle sizing, the particles may be additionally vibrated through a sieve having the desired mesh size. The particles are fed into some form of hopper 24 that directs the particles to an insulated delivery system 26. The flow of particles from the hopper 24 to the delivery system 26 is controlled or metered, such as by the particle production rate or mechanically by a gate or valve.

The properly sized particles are sucked into the high pressure delivery system 26 by venturi effect or other mechanism, such as a gate to pulse or move the particles into the delivery system 26. A power fan or compressor or high pressure gas cylinder/reservoir 28 forces a cooled high pressure carrier fluid, such as cold dry air or inert gas (such as $CO_2$, $N_2$, Ar, He, Ne), past an opening 30 through which the metered particles flow into the delivery system 26. The compressor 28 provides the force necessary to propel the particles suspended in the carrier fluid through the system 26 to the delivery tip to shoot the biocompatible crystals with desired velocity at the target skin surface. Sensors may be used to monitor the temperature, velocity, flow, and/or delivery rate of the carrier gas so that the gas flow can be controlled and adjusted to achieve the desired particle velocity at the skin surface and the desired skin resurfacing effect.

Figure 3:
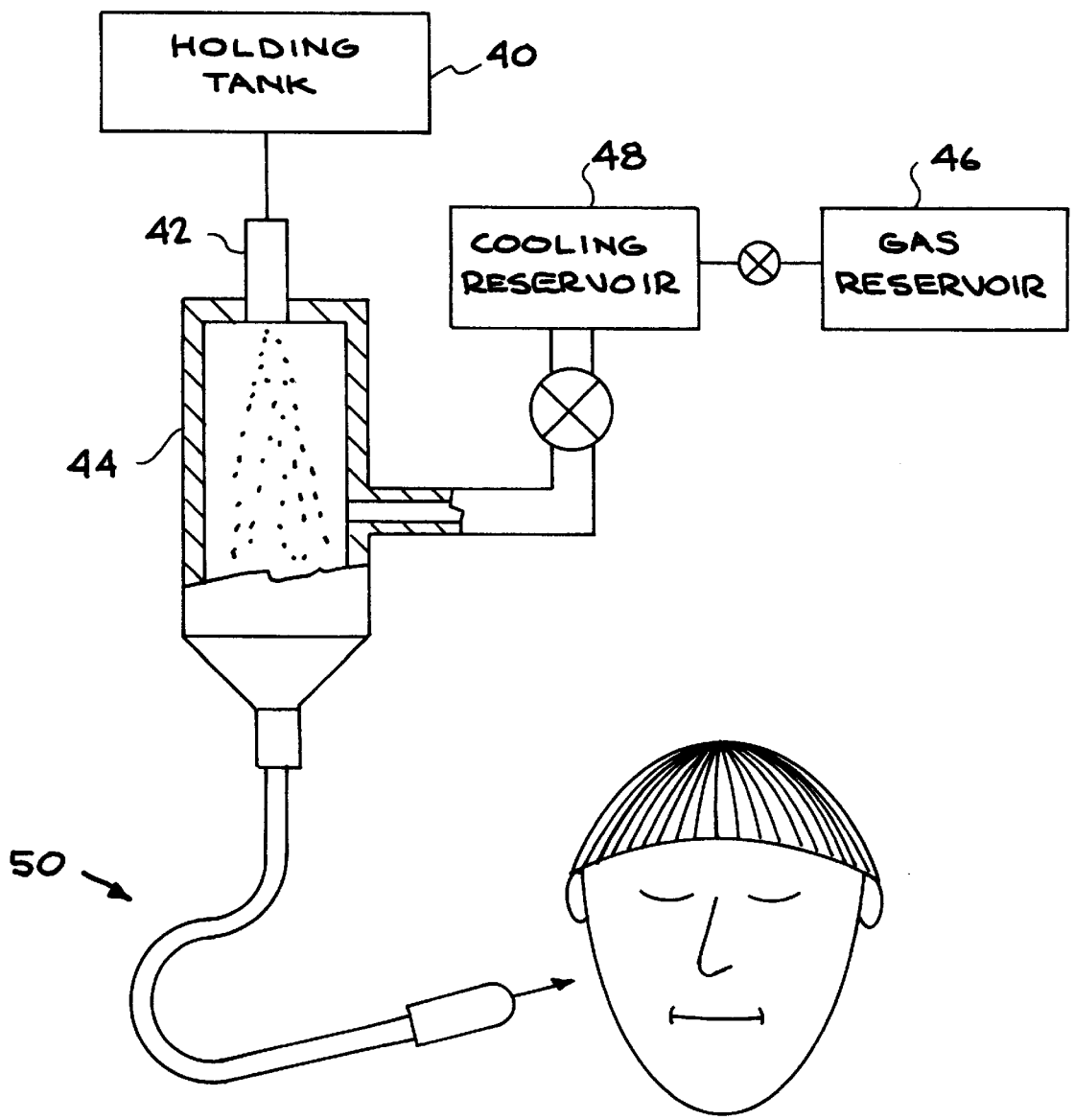
FIG. 3 shows an embodiment of an apparatus for forming a biocompatible aerosol and propelling cold particles into the delivery system.

FIG. 3 shows an alternative apparatus and method for forming the biocompatible particles. The biocompatible material is contained in a holding tank 40 in a liquid form, and optionally mixed with preservatives and additives (such as a local anesthetic and adrenaline). The liquid is released through a particle generator, such as nozzles 42 or jets (e.g., supersonic jets; piezoelectric or bubble jets such as used in ink jet printers) to form microdroplets or an aerosol of the liquid. The size and production rate of the microdroplets may be controlled. The microdroplets are sprayed into a drift chamber 44 filled with a cold carrier gas. The cooled carrier gas is introduced to the chamber 44 under pressure from a compressor or high pressure gas reservoir 46. The gas may be cooled in a cooling reservoir 48 before or after compression, and the gas temperature can be monitored and controlled. Depending on the composition of the droplets, the temperature of the gas in the drift chamber 44 can be adjusted to cause the droplets to cool or freeze and form small solid particles. The droplets or frozen particles are expelled at the desired size and rate into the delivery system 50, where they are carried to the delivery tip by the flow of cooled carrier gas. Sonication or other methods may be used to prevent condensation of the particles and clogging of the delivery tube.

In both embodiments, thermocouples may be placed along the insulated delivery system path, including at the delivery tip, to monitor the temperature of the carrier gas and biocompatible particles. The objective is to propel unmelted crystals or cold droplets at the skin; it is not desirable to have either fluid shooting out the tip or excessively cold crystals that can damage the skin. A thermostat or temperature feedback device may be beneficial to control and adjust the temperature of the particles and gas produced in the delivery system and exiting the delivery tip.

The delivery apparatus may also include an attachment to measure the surface temperature of the skin using an infrared sensor or direct thermocouple. Additionally, the delivery apparatus may include pressure sensitive sensors (e.g., spring-loaded) that allow the operator to sense and alter contour by hand-pressure. Such a device can be applied to the delivery tip, so the more pressure the operator applies, the greater the velocity and volume of shooting particles that are delivered to a certain area. Applying differential pressure is advantageous to reduce a tissue mound, lip, or edge with feedback just by operator feel. The pressure-sensitive tip can provide feedback to the carrier gas delivery and particle flow controls to increase the amount of flow carrying particles to the surface, which will increase the penetration depth.

A feedback sensor (e.g., optical) may be used to monitor the penetration depth of particles at the skin surface. The operator may be alerted by a series of audible sounds as to how fast to move the tip for maximum efficiency on a particular patient's skin. Maximum efficiency is based on the skin temperature, particle load and velocity, and type of particle shot at the skin.

The foregoing description of preferred embodiments of the invention is presented for purposes of illustration and description and is not intended to be exhaustive or to limit the invention to the precise form disclosed. Many modifications and variations are possible in light of the above teaching.

What is claimed is:

1. A method for resurfacing skin, comprising: propelling biocompatible particles at a selected velocity at a skin surface, wherein said biocompatible particles comprise biocompatible material selected from the group consisting of frozen $H_2O$ and dry ice, wherein the propulsion of said biocompatible particles is carried out using a carrier gas.

2. The method as recited in claim 1, wherein said biocompatible particles comprise at least one additive compound selected from the group consisting of a hormone, an anesthetic compound, an antibiotic, a therapeutic drug, a vaccine and mixtures thereof.

3. The method as recited in claim 2, wherein said additive compound comprises solid particles.

4. The method as recited in claim 2, wherein said additive compound comprises liquid droplets.

5. The method as recited in claim 1, wherein said carrier gas comprises a gas selected from the group consisting of dry air, nitrogen, argon, helium, neon and carbon dioxide.

6. The method as recited in claim 1, wherein the velocity of said biocompatible particles is sufficient to disrupt epidermal and dermal layers of the skin to a desired penetration depth.

7. The method as recited in claim 1, further comprising monitoring the temperature of the skin during impact of said biocompatible particles.

8. The method as recited in claim 1, further comprising forming said biocompatible particles of a size less than about 250 microns.

9. The method as recited in claim 1, further comprising forming said biocompatible particles by grinding frozen biocompatible materials.

10. The method as recited in claim 1, further comprising forming said biocompatible particles by injecting microdroplets of said biocompatible material into said carrier gas.

11. The method as recited in claim 1, further comprising monitoring the temperature and pressure of said carrier gas.

12. The method as recited in claim 1, further comprising controlling the size of said biocompatible particles.

13. The method as recited in claim 1, further comprising controlling the flow of said carrier gas.

14. The method as recited in claim 1, further comprising monitoring the flux of said biocompatible particles on the skin.

15. The method as recited in claim 1, wherein said biocompatible particles comprise drugs for treatment of pre-cancerous or cancerous skin legions.

16. The method as recited in claim 1, wherein said carrier gas propels said biocompatible particles at a pressure greater than atmospheric pressure.

17. The method of claim 1, further comprising cooling said carrier gas.

* * * * *